United States Patent [19]

Rosen et al.

[11] Patent Number: 5,797,887
[45] Date of Patent: Aug. 25, 1998

[54] MEDICAL DEVICE WITH A SURFACE ADAPTED FOR EXPOSURE TO A BLOOD STREAM WHICH IS COATED WITH A POLYMER CONTAINING A NITROSYL-CONTAINING ORGANO-METALLIC COMPOUND WHICH RELEASES NITRIC OXIDE FROM THE COATING TO MEDIATE PLATELET AGGREGATION

[75] Inventors: Gerald M. Rosen, Lutherville; William R. Herzog, Jr.; Sovitj Pou, both of Baltimore, all of Md.

[73] Assignee: Novovasc LLC, Baltimore, Md.

[21] Appl. No.: 703,646

[22] Filed: Aug. 27, 1996

[51] Int. Cl.$^6$ ............................. A61M 5/32; A61M 25/00
[52] U.S. Cl. .................. 604/265; 604/266; 424/425; 623/2
[58] Field of Search ........................ 604/49, 50, 264, 604/265, 266; 424/424, 425; 623/1

[56] References Cited

U.S. PATENT DOCUMENTS

| | | |
|---|---|---|
| 5,278,192 | 1/1994 | Fung et al. . |
| 5,366,997 | 11/1994 | Keefer et al. . |
| 5,370,614 | 12/1994 | Amundson et al. . |
| 5,380,758 | 1/1995 | Stamler et al. . |
| 5,405,919 | 4/1995 | Keefer et al. . |
| 5,428,070 | 6/1995 | Cooke et al. . |
| 5,441,947 | 8/1995 | Dodge et al. . |
| 5,457,113 | 10/1995 | Cullinan et al. . |
| 5,462,937 | 10/1995 | Cullinan et al. . |
| 5,470,307 | 11/1995 | Lindall . |
| 5,482,925 | 1/1996 | Hutsell . |
| 5,492,926 | 2/1996 | Cullinan et al. . |
| 5,523,092 | 6/1996 | Hanson et al. ............ 604/96 |
| 5,525,357 | 6/1996 | Keefer et al. . |
| 5,536,241 | 7/1996 | Zapol ...................... 604/48 |
| 5,591,227 | 1/1997 | Dinh et al. . |
| 5,599,352 | 2/1997 | Dinh et al. ............ 606/195 |
| 5,605,696 | 2/1997 | Eury et al. ............ 424/423 |

FOREIGN PATENT DOCUMENTS

| | | |
|---|---|---|
| 95-07691 | 3/1995 | WIPO . |
| 96/35416 | 11/1996 | WIPO . |
| 96/38136 | 12/1996 | WIPO . |

OTHER PUBLICATIONS

Hobel, et al, Summary: Sodium Nitroprusside: its toxicity, metabolism, and organic distribution, Herz1 (1976), 130–136(Nr.2).

(List continued on next page.)

*Primary Examiner*—Mark Bockelman
*Assistant Examiner*—Jennifer R. Sadula
*Attorney, Agent, or Firm*—Millen, White, Zelano & Branigan, P.C.

[57] ABSTRACT

A surface of a foreign body exposed to the flowing blood of a living being which normally would promote the aggregation of platelets in that blood to form a layer affixed to that surface and thus restrict the flow of blood past that surface or to form a blood clot detachable from that surface which when detached could trigger a stroke, heart attack or partial loss of organ function, such as plastic tubing, a balloon or the end of a catheter surgically inserted in a blood vessel or a stent implanted therein, e.g., in conjunction with percutaneous transluminal coronary angioplasty or the interior wall of a length of plastic tubing used to transport the blood of a patient, undergoing hypothermic surgery or dialysis, inhibits such aggregation when that surface is coated with a physiologically acceptable polymer, such as polyvinyl alcohol or polyvinyl chloride, containing dissolved or dispersed therein a nitrosyl-containing organometallic compound, whether ionic salt or chelate, which slowly decomposes at the body temperature and in so doing releases a platelet aggregation-inhibiting amount of nitric oxide during either the post-surgical period when the individual is a high risk candidate for post-surgical foreign body-mediated platelet aggregation on or at the situs of the foreign body or during dialysis of the blood to remove waste in those individuals with dysfunctional kidneys.

16 Claims, 2 Drawing Sheets

OTHER PUBLICATIONS

Furchgott, et al., The obligatory role of endothelial cells in the relaxation of arterial smooth muscle by acetylcholine, Nature vol. 288, 27 Nov. 1980.

Palmer et al., Medical Intelligence–Drug Therapy—Sodium Nitroprusside, The New England Journal of Medicine, Feb. 6, 1975.

Palmer et al., Nitric oxide release accounts for the bilogical activity of endothelium–derived relaxing factor, Nature vol. 327, Jun. 11, 1987.

Snyder et al., Biological Roles of Nitric Oxide, Scientific American, May 1992.

Moncada et al., The L–Arginine—Nitric Oxide Pathway, The New England Journal of Medicine, Dec. 30, 1993.

Noack et al., Molecular Aspect Underlying the Vasodilator Action of Molsidomine, Journal of Cardiovascular Pharmacology, vol. 14 (Suppl. 11) 1989.

Ignarro et al., Mechanism of Vascular Smooth Muscle Relaxation by Organic Nitrates, Nitrites, Nitroprusside and Nitric Oxide: Evidence for the Involvement of S–Nitrosothiols as Active Intermediates, The Journal of Pharmacology and Experimental Therapeutics, vol. 218, No. 3, 1981.

Kowaluk et al, Spontaneous Liberation of Nitric Oxide Cannot Account for in Vitro Vascular Relaxation by S–Nitrosothiols, The Journal of Pharmacology and Experimental Therapeutics, vol. 255, Nov. 1, 1990.

Maragos et al., Complexes of 'NO with Nucleophiles as Agents for the Controlled Biological Release of Nitric Oxide. Vasorelaxant Effects. J. Med. Chem. 1991, 34–3242.

Bates et al., Nitric Oxide Generation From Nitroprusside By Vascular Tissue. Evidence That Reduction Of The Nitroprusside Anion And Cyanide Loss Are Required, Biological Pharmacology, vol. 42, Suppl. pp. S157–S1G5, 1991.

Makings et al., Caged Nitric Oxide, Stable Organic Molecules From Which Nitric Oxide Can Be Photoreleased, The Journal of Biological Chemistry, vol. 269, No. 9, Issue of Mar. 4, pp. 6282–6285, 1994.

Packer, et al, Rebound Hemodynamic Events After The Abrupt Withdrawal of Nitroprusside In Patients With Severe Chronic Heart Failure, The New England Journal of Medicine, vol. 301, No. 22, Nov. 29, 1979.

Ivankovich et al., Nitroprusside and Other Short–Acting Hypotensive Agents—Sodium Nitroprusside: Metabolism And General Considerations, International Anesthesiology Clinics, vol. 16 No. 2, Summer 1978.

Sessa et al., The metabolism of L–arginine and its significance for the biosynthesis of endothelium–derived relaxing factor: L–Glutamine inhibits the generation of L–arginine by cultured endothelial cells, Proc. Natl. Acad. Sci. USA vol. 87, pp. 8607–8611, Nov. 1990.

Kreye et al., Possible Site of the in vivo Disposition of Sodium Nitroprusside in the Rat, Naunyn–Schmiedeberg's Arch Pharmacol (1982) 320: 260–265.

Munson et al., Principles of Pharmacology Basic Concepts & Clinical Applications, Chapman & Hall, pp. 482–483, 556.

Bogdansky, Natural Polymers as Drug Delivery Systems, Biodegradable Polymers as Drug Delivery Systems, Editors Chasin et al., Marcel Dekker, Inc., New York.

Green et al., Analysis of Nitrate, Nitrite, and [15N]Nitrate in Biological Fluids, Analytical Biochemistry 126, 131–138 (1982).

Bailey, Coating of Endovascular Stents Chap 44., Textbook of Interventional Cardiology, vol. 2 Editor Topol, W.B. Saunders Company 1984.

Byron et al., Effects of Heat Treatment on the Permeability of Polyvinyl Alcohol Films to a Hydrophilic Solute, Journal of Pharmaceutical Sciences, vol. 76, No. 1 Jan. 1987.

Lewis, Controlled Release of Bioactive Agents from Lactide/Glycolide Polymers, Biodegradable Polymers as Drug Delivery Systems, Editors Chasin et al., Marcel Dekker, Inc., New York.

Hobel, et al., Summary: Studies on the Metabolism and Distribution of 14 C–Sodium Nitro–prusside in Rats.

MEDICAL DEVICE WITH A SURFACE ADAPTED FOR EXPOSURE TO A BLOOD STREAM WHICH IS COATED WITH A POLYMER CONTAINING A NITROSYL-CONTAINING ORGANO-METALLIC COMPOUND WHICH RELEASES NITRIC OXIDE FROM THE COATING TO MEDIATE PLATELET AGGREGATION

FIELD OF THE INVENTION

This invention relates generally to novel entrapment of nitric oxide-releasing metal compounds, whether salts or complexes into drug delivery systems and methods for using them, more particularly for the prevention of restenosis after percutaneous transluminal coronary angioplasty, and for the prevention of acute or subacute thrombotic occlusion related to the use or deployment of a synthetic device within the vascular tree.

DESCRIPTION OF THE PRIOR ART

Nitroprusside and similar nitrosyl-containing organometallic compounds, whether ionic salts or chelates, have been known since the mid-1950's to exhibit short-term hypotensive effects. The mechanism by which this drug elicited its pharmacological activity was not known until the discovery that endothelial cells secreted a factor, which regulated vascular tone, termed Endothelial-Derived Relaxation Factor (EDRF) (Furchgott and Zawadzki, *Nature*, 288: 373–376, 1980). In 1987, Palmer and co-workers (*Nature*, 327: 524–526, 1987) determined that the free radical, nitric oxide, mimicked many of the physiologic properties reported for EDRF. Besides regulating vascular tone, nitric oxide has been found to: (a) inhibit neutrophil adhesion, (b) antagonize platelet aggregation and (c) enhance macrophage-mediated microbial killing (see, S. H. Synder and D. S. Bredt, *Sci. Amer.* 68–77, May 1992; S. Moncada and A. Higgs, *New Engl. J. Med.* 329: 2002–2012, 1993).

Without question nitric oxide is a physiologic messenger, whose control of a myriad of functions makes this free radical an essential ingredient for maintaining normal life processes. However, the pharmacological applications of nitric oxide are limited, as systemic use can frequently result in severe toxicity. For instance, administration of gaseous nitric oxide systemically to treat localized abnormalities or diseases is contraindicated, because the control of its dosage in the therapeutic range cannot easily be achieved. Even if it were possible to carefully titrate the gaseous dose of nitric oxide to minimize systemic toxicity, it would be very difficult to locally administer this drug to sites of interest. Therefore, the development of therapeutic agents, which would mimic the pharmacological action of nitric oxide, has received considerable attention. Several classes of nitric oxide-releasing compounds have been developed, including syndnoeimine (Noack and Feelisch, *J. Cardiovasc. Pharmacol.* 14S: 51–55, 1989), nitroglycerin (Noack and Feelisch, *J. Cardiovasc. Pharmacol.* 14S: 51–55, 1989), S-nitroso derivatives (Ignarro, Lippton, Edwards, Baribos, Hyman, Kadowitz and Gretter, *J. Pharmacol. Exp. Ther.* 218: 739–729, 1981; Kowaluk and Fung, *J. Pharmacol. Exp. Ther.* 255: 1256–1254, 1990; Stamler, Loscalzo, Slivka, Simon, Brown and Drazen, U.S. Pat. No. 5,380,758, 1995) and N-nitroso compounds (Maragos, Morley, Wink, Dunams, Saavedra, Hoffman, Bove, Issac, Hrabie and Keefer, *J. Med. Chem.* 34: 3242–3247, 1991; Keefer, Dunams and Saavedra, U.S. Pat. No. 5,366,997, 1994; Keefer and Hrabie, U.S. Pat. No. 5,405,919, 1995). These compounds require either hydrolysis or metabolic activation, through either oxidation or reduction, to generate nitric oxide. Alternatively, several studies have reported on the development of photolyzed "caged-nitric oxide" compounds. For example, the organometallic-containing compound nitroprusside has been found to release nitric oxide upon light activation (Bates, Baker, Guerra and Harrison, *Biochem. Pharmacol.* 42S: S157–S165, 1991). Contrary to this, nitric oxide generation from light activation of ruthenium nitrosyl trichloride failed to inhibit platelet aggregation, thereby questioning the utility of this approach (Makings and Tsien, *J. Biol. Chem.* 269: 6282–6285, 1994).

Clinically, nitroprusside is used therapeutically to treat hypertension acutely, as this nitric oxide releasing compound has a short lifetime of several minutes in blood (Palmer and Lasseter, *New Engl. J. Med.* 292: 294–297, 1975; Packer, Meller, Medine, Gorlin and Herman, *New Engl. J. Med.* 301: 1193–1197, 1979). The degradation of nitroprusside is thought to arise through reductive processes taking place in the bloodstream. Even though it has been suggested that sulfhydryl groups attached to endothelial cells lining the vascular walls might initiate this reaction, other reductants such as glutathione or ascorbic acid may likewise contribute to its unusually short physiologic lifetime (Höbel, Kreye and Raithelhuber, *Herz.* 1: 130–136, 1976; Ivankovitch, Miletich and Tinker, *Int. Anesthesiol. Clin.* 16: 1–29, 1978; Kreye and Reske, *Arch. Pharmacol.* 320: 260–265, 1982). Based on this pharmacological behavior, the clinical use of this drug requires that it be given continuously, as suspension of its use rapidly results in diminished drug efficacy concomitant with an increase in blood pressure.

Apparatuses and methods have been developed for delivering nitric oxide-releasing compounds and other drugs selectively and locally to a specific internal body site, e.g., for preventing restenosis after percutaneous transluminal coronary angioplasty. For instance, Cooke, Dzau and Gibbons (U.S. Pat. No. 5,428,070, 1995) described the use of orally administered L-arginine as a dietary supplement to enhance nitric oxide production by providing the substrate to nitric oxide synthase, the enzyme which metabolizes L-arginine to L-citrulline and nitric oxide. This would not be applicable to restenosis, since in this pathology, the endothelial cell levels of L-arginine are not diminished, but rather the specific isoform of nitric oxide synthase localized in endothelial cells is dysfunctional. Furthermore, even if levels of L-arginine were low, replacement therapy through supplementation of dietary L-arginine is an inappropriate treatment as cellular sources of L-arginine arise primarily from the reverse metabolism of L-citrulline to L-arginine (Sessa, Hecker, Mitchell and Vane, *Proc. Natl. Acad. Sci. USA*, 87: 8607–8611, 1990).

An additional example comes from U.S. Pat. No. 5,282,785, which employs a drug delivery apparatus, comprising a flexible catheter for insertion into an internal target area of the body and a drug delivery means connected to the catheter. In this version, the latter delivers the drug in a radially restricted manner and comprises (a) a drug delivery chamber at the distal end of the drug delivery apparatus, which has a selectively permeable outer membrane portion and circumferential lips adjacent to both the proximal and distal ends of the drug delivery system to minimize movement of a drug beyond a segment of internal tissue and a fluid delivery passageway extending from the chamber to the proximal end of the catheter; and (b) a non-permeable balloon affixed to and surrounding a portion of the chamber; which, when inflated, secures the chamber at the target area and radially restricts local delivery of the drug by providing intimate contact between balloon and a portion of the internal body tissue. The use of such an indwelling catheter devices is limited to short term applications (usually no longer than 10-20 minutes), because they obstruct arterial blood flow. The apparatus also includes means of assisting the transport of the drug across the selectively permeable outer membrane with or without application of pressure.

Similarly, U.S. Pat. No. 5,286,254, which also employs an apparatus, comprising a flexible catheter having a distal end and a proximal end and which is adapted for insertion into an internal area of a body; a drug delivery means having a fluid delivery passageway for delivering a drug to the distal end of the apparatus, an outer wall and a selectively permeable microporous outer membrane portion proximate to the distal end and an impermeable end to enhance delivery of the drug to the target area; and phoresis means for assisting the transport of the drug across the selectively permeable membrane.

These types of apparatuses have several disadvantages, as do most intravascular devices, by promoting platelet deposition at the site where the device is located, as is the case of stents or after removal of a device at a vascular site, which has received treatment with either a balloon angioplasty or delivery device as described in U.S. Pat. No. 5,282,785 and U.S. Pat. No. 5,286,254.

U.S. Pat. No. 5,370,614 describes the employment of a sheath coated with a matrix-containing a drug and placed over the balloon of a balloon catheter. When placed at the point of treatment, the balloon is expanded and the sheath bursts from the pressure applied, releasing the drug as a bolus at the site of interest. Because restenosis occurs over weeks, treatment would likely require the slow presentation of nitric oxide over an extended period of time, the teaching presented in U.S. Pat. No. 5,370,614 cannot be applied to this disease condition.

U.S. Pat. No. 5,470,307 describes the use of a coating to an apparatus to which a drug is covalently bonded to a substrate on the exterior surface of a catheter using a linker, which photolytically releases the agent upon exposure to light source at an appropriate wavelength. The necessity to photolytically break a chemical bond in order to release nitric oxide has a clear disadvantage as there is no continued light source in the blood stream to cleave the linker molecule, thereby releasing nitric oxide for extended periods of time.

U.S. Pat. No. 5,278,192 describes the continual use of organic nitrites as vasodilator therapy on a chronic basis for 24 hours without developing tolerance. The necessity of organic nitrites to be metabolized by endothelial cells, which have been made dysfunctional as the result of a disease state, would not provide a continued flux of nitric oxide to prevent restenosis and/or platelet aggregation (Munson, "Principles of Pharmacology—Basic Concepts & Clinical Applications", pp. 482–483, 1995). Furthermore, as regulating vascular tone is not the primary purpose of this patent application, but rather the local control of platelet aggregation and initial proliferation, leading to restenosis, altering systemic vascular tone through administration of either nitric oxide or a nitric oxide-releasing pro-drug is contraindicated.

The method of this invention provides a method of decreasing platelet aggregation, either in the form of a layer that builds up on a medical device that is permanently implanted in a blood vessel or that comes in contact with the circulating blood of a living being on a temporary basis or in the form of a detachable clot which, if it travels to the organs such as brain, lung, heart, kidney and liver, can be debilitating or have life threatening sequelae. This method also applies to intravascular devices, either temporary or permanent, or to extracorporeal synthetic circuits, such as cardiopulmonary bypass or kidney dialysis.

SUMMARY OF THE INVENTION

In a method aspect, this invention relates to an approach for the prevention of the aggregation of platelets from blood flowing in a living being resulting from exposure of the blood to a foreign body, which comprises coating the surface of the foreign body that contacts the blood prior to contact therewith, with a physiologically acceptable polymer which contains dissolved or dispersed therein an amount of a nitrosyl-containing organometallic compound, whether an ionic salt or a chelate, which slowly decomposes at body temperature and in so doing releases an amount of nitric oxide from the coating effective to inhibit the platelet aggregation which would otherwise be promoted by the foreign body.

Furthermore, this invention relates to an approach for the prevention of restenosis—a gradual re-occlusion of the blood vessel over a prolonged period time frequently occurring after 1–2 weeks—by coating the surface of the foreign body, known in the profession as a stent, that contacts the blood with a physiological acceptable polymer which is insoluble in the blood and which contains dissolved or dispersed therein an amount of a nitrosyl-containing organometallic compound, whether an ionic salt or a chelate, which slowly decomposes at body temperature and in so doing releases an amount of nitric oxide locally from the coating effective to inhibit restenosis.

In a composition of matter aspect, this invention relates to an aqueous liquid coating composition comprising (a) an aqueous vehicle; (b) an injectable physiologically acceptable polymer dissolved or dispersed in the vehicle; and (c) a nitrosyl-containing organometallic compound, whether an ionic salt or a chelate, which slowly decomposes at body temperature and in so doing releases nitric oxide, wherein the polymer is precipitable from the aqueous vehicle, e.g., through evaporation of the aqueous vehicle, and the concentration of a nitrosyl-containing organometallic compound, whether an ionic salt or a chelate in the aqueous vehicle is effective to generate a platelet aggregation-inhibitory effect and restenosis-inhibitory effect when the polymer with the nitrosyl-containing organometallic compound, whether an ionic salt or a chelate occluded therein is deposited on a platelet aggregation promoting surface within the body of a living being.

In an article of manufacture aspect, this invention relates to an intravascular medical device, such as a balloon or catheter tip adapted for insertion or a stent adapted for implantation into the inner wall of a blood vessel, e.g., in conjunction with percutaneous transluminal angioplasty, whose surfaces which are in contact with the blood stream of a living being are coated with a coating of a physiologically acceptable polymer which is insoluble in blood and which contains dissolved or dispersed therein an amount of a nitrosyl-containing organometallic compound, whether an ionic salt or a chelate, which slowly decomposes at body temperature over a prolonged period and in so doing releases nitric oxide at a rate effective to prevent platelet aggregation which could otherwise occur when the stent is implanted in a blood vessel.

In another article of manufacture aspect, this invention relates to an extravascular medical device, such as plastic tubing or membranes whose surfaces which are in contact with the blood stream of a living being are coated with a physiological acceptable polymer which is insoluble in blood or a plastic tubing which contains dissolved or dispersed within the plastic tubing an amount of a nitrosyl-containing organometallic compound, whether an ionic salt or a chelate, which slowly decomposes at body temperature over a prolonged period of time and in so doing releases nitric oxide at a rate effective to prevent platelet aggregation which could otherwise occur as the result of blood coming in contact with the plastic tubing or membranes.

In another article of manufacture aspect, this invention relates to a medical device, such as plastic tubing or membranes, e.g., a vascular graft, whose surfaces which are in contact with the blood stream of a living being are sequentially coated with first, a nitrosyl-containing organometallic compound, whether an ionic salt or chelate, which slowly decomposes at body temperature over a prolonged period of time releasing nitric oxide at a rate effective to prevent platelet aggregation which could otherwise occur as the result of blood coming into contact with the plastic tubing or membrane and second, a physiologically acceptable semi-permeable membrane which is insoluble in blood which allows the passive diffusion of nitric oxide from the first layer into the bloodstream.

DETAILED DESCRIPTION OF THE PREFERRED EMBODIMENTS

Figure 1:
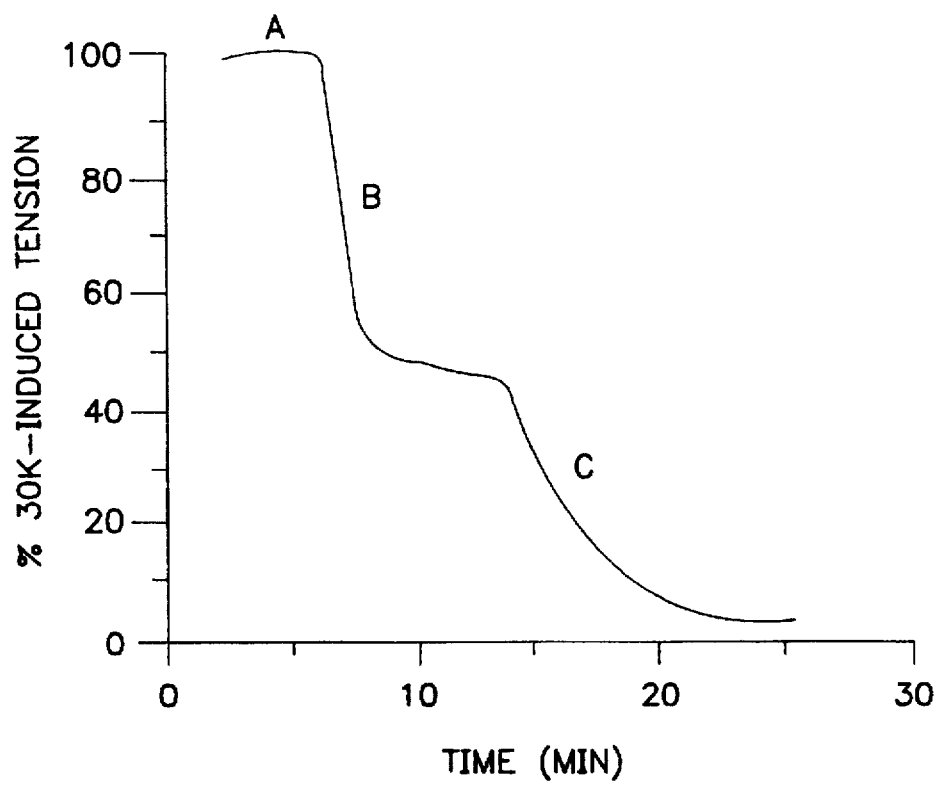
FIG. 1 is a graph of change in isometric tension through treated and untreated tubing.

This invention is based on the discovery that the aggregation of platelets in blood as a result of exposure of the blood to a foreign body or to the injured endothelium can be inhibited by coating at least the surface of the foreign body to which the circulating blood is exposed with a coating containing an amount of a nitrosyl-containing organometallic compound, whether an ionic salt or a chelate, which is stable at room temperature but at body temperature in blood releases from the coating a platelet-aggregating-inhibiting amount of nitric oxide, which amount achieves a nitric oxide concentration locally at the surface of the foreign body which cannot safely be achieved by the administration of a nitrosyl-containing organometallic compound, whether an ionic salt or a chelate given systemically, whether per se, by intramuscular injection, intravenous infusion or by injection directly into the blood vessel itself.

One Example of such a nitrosyl-metal chelate is nitroprusside in which the iron ion is complexed to five cyano groups.

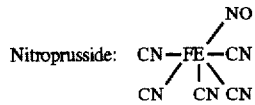

The sixth ligand position is occupied by a nitrosyl group. Exposure of polymer encapsulated nitroprusside to aqueous solutions including blood releases nitric oxide. The enhanced stability of nitroprusside in this polymer compared to the short lifetime of this agent in blood is the result of the inability of blood-containing reductants such as thiols and ascorbic acid to diffuse through the small pores of the polymer to inactivate nitroprusside by rapid decomposition with regard to its release of nitric oxide.

Other suitable complexing agents for the iron ion are ethylenediaminetetraacetic acid, EDTA; diethylenetriaminepentaacetic acid, DTPA and many others of this class of chelates; 1,4,7,10-tetraazacyclododecane-N,N',N", N'"-tetraacetic acid, DOTA and trans-1,2-cyclohexylenediamine-N,N,N', N'tetraacetic acid and many others of this class of chelates. The invention may also be practiced with suitable complexing agents for other metal ions.

This invention relates to methods, compositions and articles of manufacture useful in the prevention of platelet deposition either on a foreign body introduced surgically into a blood vessel or at vascular sites which have received treatment, e.g., balloon angioplasty with stent implantation. The reduction of platelet deposition has important implications for reducing the likelihood of the phenomenon of restenosis occurring following balloon angioplasty. By impregnating the polymer used to coat an implantable intravascular device such as a metal stent with a nitrosyl-containing organometallic compound, whether an ionic salt or a chelate, nitric oxide can be locally delivered at a low dose which can be controlled by varying the concentration of the nitrosyl-containing organometallic compound, whether an ionic salt or a chelate, and the nature of the polymer forming the coating on the implantable intravascular device. With such an approach, systemic nitric oxide toxicity, e.g., hypotension, can be prevented from occurring.

Nitrosyl-containing organometallic compounds, whether ionic salts or chelates employed in the composition of this invention are:

(a) non-toxic, that is, substantially free from any significant toxic effects at their effective applied concentration;

(b) substantially free of sympotomology, that is, they do not produce significant symptoms detectable to the person treated at their effective applied concentration;

(c) relatively stable at room temperature in an aqueous environment, away from light, i.e., once a nitrosyl-metal chelate is impregnated into a polymer and coated onto a stent or tubing or other device, or impregnated into a tubing, nitric oxide is not released therefrom at a significant rate. For example, during the preparation of the coating or its application to the stent, tubing or other device or thereafter, or during self storage in a packaged container, nitric oxide may be released at a rate no greater than 1% per month;

(d) long lasting, that is, once a stent, tubing or other intra- or extravascular device bearing on the surface thereof the polymer impregnated with the nitrosyl-containing organometallic compound, whether an ionic salt or a chelate comes in contact with blood or is inserted into a blood vessel, the duration of the delivery of nitric oxide can be adjusted by varying the concentration of the nitrosyl-containing organometallic compound, whether an ionic salt or a chelate in the polymer to conform to the clinical situation to be a matter of minutes, e.g., 5–90 minutes in the case of a angioplasty balloon or catheter, hours, e.g., 1–4 hours in the case of hypothermic surgery blood circulation, cardiopulmonary bypass or dialysis of blood passing though plastic tubing, days to weeks, e.g., 1–14 days or longer, in the case of a stent.

The nitrosyl-containing organometallic compound, whether an ionic salt or a chelate employed in this invention, are compounds of the formula $|MX_5NO|^{-2}\ Y^{+2}$ or $2Y^{+1}$; where M is a transition metal such as Fe, Co, Mn; X is a negatively charged ion such as CN, Cl, Br, I, or chelates such as EDTA, DTPA that at physiologic pH have negatively charged carboxylic acid groups; and Y is a positively charged salt.

The nitrosyl-containing organometallic compound, whether an ionic salt or a chelate must be incorporated into a polymer with pores sufficiently small to inhibit the diffusion of blood-borne reductants from entering the polymer and thereby inactivating the nitric oxide releasing compound of this invention, yet large enough to allow the passive diffusion of nitric oxide from inside the polymer to the bloodstream.

The coating on the foreign body preferably is from 0.1–1.0 mm thick and contains 1 µmole to 100 mmoles of a nitrosyl-containing organometallic compound, whether an ionic salt or a chelate, per $mm^2$. Higher concentrations are desirable when the diffusion rate of the nitric oxide from the polymer is very slow or when it is desired that the release of the nitric oxide occurs over a prolonged period of time, e.g., more than 48 hours.

A wide variety of polymers can be used to encapsulate nitroprusside and other nitrosyl-containing organometallic compounds, whether ionic salts or chelates, including both physiologically inert and biodegradable polymers and those which are only slowly soluble and those which are insoluble in blood. Insoluble polymers which are suitable are those which form a permeable membrane coating around the foreign body so that the nitric oxide can migrate therefrom as it is produced. When the foreign body is inserted into the living being, it preferably is physiologically inert and, when permanently implanted, also biodegradable. Examples of biodegradable polymers which can be used as drug delivery systems include the natural polymers: (1) collagen, (2) albumin, (3) casein, (4) fibrin and (5) gelatin (S. Bogdansky, in: Biodegradable Polymers as Drug Delivery Systems, ed. by M. Chasin and R. Langer, Marcel Dekker,. Inc. New York, pp. 231–259, 1990). Synthetic polymer systems include: (1) polyactide and polyglycodide (D. H. Lewis, in: Biodegradable Polymers as Drug Delivery Systems, ed. by M. Chasin and R. Langer, Marcel Dekker,. Inc. New York, pp. 1–42, 1990); polyvinyl alcohols (P. R. Byron and R. N. Dalby, J. Pharm. Sci. 76: 65–67, 1987); polyalkylene oxides and polyvinyl chloride.

Characteristics of an "ideal" coating for a stent is one which can be applied to luminal or subluminal surfaces, does not cause a significant increase in stent wall thickness; is stable over time without desquamation; has a surface tension below 30 dyne/cm; has a smooth surface texture (<1 µm irregularities) has a negative or neutral surface charge; allows rapid endothelialization; permits timed elution of the nitric oxide; and delivers an effective concentration locally of the nitric oxide (S. R. Bailey, "Coating of Endovascular Stents" in: Textbook of Interventional Cardiology, ed. by E. J. Topol, Vol. 2, 2nd edition, W. B. Saunders, Philadelphia, pp. 754–765, 1994).

The desired coating can be formed by immersing the foreign body in a solution or colloidal dispersion of the selected polymer in an aqueous vehicle with the nitrosyl-containing organometallic compounds, whether ionic salts or chelates, and then insolubilizing the polymer, e.g., by changing the pH or the ionic strength or through evaporation of the solvent or by denaturing a proteinaceous polymer, so that a coating of the polymer with the nitrosyl-containing organometallic compounds, whether ionic salts or chelates, occluded therein deposits on the exposed surfaces of the foreign body. For example, a stent is placed in an aqueous solution of polyvinyl alcohol with the nitrosyl-containing organometallic compounds, whether ionic salts or chelates. The surface of the stent is thereby coated with a nitrosyl-containing organometallic compound, whether ionic salt or chelate dissolved in polyvinyl alcohol. Upon evaporation of the aqueous solution, the polymer encasing the nitric oxide releasing compound is precipitated onto the surface of the stent. The rate at which nitric oxide is released when the stent is exposed to blood can be determined by placing the coated stent in phosphate buffer, pH 7.4, using the Griess reaction (Green, Wagner, Giogowski, Skipper, Wishnok and Tannebaum, Anal. Biochem., 126: 131–138, 1982).

The foreign body can be any medical device or product which has a surface which is exposed to the blood stream of a living human being and is susceptible to or which promotes platelet aggregation. Intravascular devices and angioplasty surgery in general frequently promotes platelet adhesion and aggregation. Placement of stents into a living human being can also promote platelet aggregation and subsequent restenosis. Local delivery of nitric oxide can ameliorate these life-threatening conditions. Similarly, patients undergoing blood flow diversion outside the body, e.g., in conjunction with hypothermic surgery utilizing cardiac and/or pulmonary bypasses and dialysis of organs such as the kidney, have increased susceptibility to platelet aggregation due to a foreign body response resulting from the exposure of the blood to the plastic tubing or membranes used to transport the blood. A similar risk of foreign body response occurs in patients undergoing angiograms as a result of the insertion of plastic tubing into an artery. Therefore, anticoagulants are conventionally administered (with unavoidable associated risks) to suppress this response. When the interior of the tubing is coated with coating according to this invention, anticoagulants can be reduced or even eliminated entirely. Synthetic or reconstituted natural, e.g., from powdered bone and binder, bony structures can also trigger a foreign body response and therefore can benefit from a coating thereon according to this invention. A preferred embodiment of the intravascular device aspect of this invention is metal, e.g., stainless steel or polymeric, intravascular stent which typically is implanted temporarily or permanently in a blood vessel after percutaneous transluminal coronary angioplasty.

In another embodiment of the invention, the interior surfaces of a plastic tubing or membrane, e.g., a vascular graft, consisting of an impermeable material such as dacron or expanded polytetrafluoroethylene (Goretex), is sequentially layered with first, a nitrosyl-containing organometallic compound, such as nitroprusside, and second, a semipermeable membrane, such as expanded polytetrafluoroethylene, wherein the pores of the semipermeable membrane are sufficiently small to inhibit the diffusion of blood-born reductants from penetrating through the membrane, yet large enough to allow the passive diffusion of nitric oxide from the first layer into the bloodstream.

From the foregoing description, one skilled in the art can easily ascertain the essential characteristics of this invention, and without departing from the spirit and scope thereof, can make various changes and modifications of the invention to adapt it to various usage and conditions. The entire disclosures of all applications, patents and publications, cited above and below are incorporated by reference. The following preferred specific embodiments are, therefore, to be construed as merely illustrative and not limitative of the disclosure in anyway whatsoever.

EXAMPLES

Example 1

Preparation of Nitric Oxide Delivery Systems. A 5% (w/w) of polyvinyl alcohol (PVA, 99% hydrolyzed, M.W.

124,000–186,000) solution was prepared by dissolving PVA in distilled water at 100° C. After this PVA solution was prepared, it was cooled to room temperature to which nitroprusside (SNP) was added to reach a final concentration of 10 μM. Polyvinyl chloride tubing was coated with either PVA-containing SNP or PVA-without SNP by allowing the selected solution to flow through the tubing. After air drying the tubing the coating process can be repeated a number of times to obtain the desired flux of nitric oxide. Once the desired release rate of nitric oxide is achieved, PVA—without SNP was placed over the dried PVA-containing SNP. In this manner, SNP is protected by the coating of PVA—without SNP from blood elements, which rapidly inactivate SNP. Other surfaces were coated in a similar manner such as plastic Falcon tubes or glass coverslips.

Example 2

Chemical Assay for Nitric Oxide. The Griess Reaction was used to determine nitric oxide concentration. As this assay can only estimate nitric oxide release in the μmolar range, high concentrations noted above were used. Using the standard Griess Reaction (Green, Wagner, Giogowski, Skipper, Wishnok and Tannebaum, Anal. Biochem. 126: 131–138, 1982), the flux of nitric oxide release can be measured and compared to bioassay procedures. Typically, 30 mL of 0.1M phosphate buffer, pH 7.5, was placed into PVA-without SNP and PVA-containing SNP coated tubing or Falcon tube, kept at room temperature or at 37° C. in room light. Samples (0.6 mL) were taken every 24 hr and added to freshly prepared Griess's reagent (0.4 mL of 0.1% N-(1-naphthyl)ethylenediamine in water and 1% sulfanilamide in 5% phosphoric acid mixed 1:1). This reaction incubates for 15 minutes at room temperature and absorbance is recorded at 550 nm. Concentrations of nitrite were estimated by comparing absorbances at 550 nm against standard solutions of sodium nitrite prepared in the same buffer.

Example 3

Biologic Assays for Nitric Oxide—Tension Measurement. Using the method of Furchgott and Zawadzki (Nature, 288: 373–376, 1980), aortic and pulmonary rings were isolated and two stainless steel hooks (0.1 mm diameter) were inserted through the lumen of the isolated artery rings. One hook was fixed to the bottom of the tissue chamber (7.5 mL in size), the other hook was connected to an isometric force transducer (Model 52-9529, Harvard Apparatus, South Natick, Mass.), which was mounted directly above the tissue chamber. Isometric tension was continuously monitored and recorded on a strip chart recorder. The tissue was superfused at a rate of 2.5 mL/min with modified Krebs solution (MKS). Resting passive tension was maintained at 600–650 mg throughout the experiment. After 60–90 minutes of equilibration, artery rings were exposed to 30 μM K+ solution three times to stabilize a response (FIG. 1, point A). At this point, the perfusion tubing, coated with PVA alone, was replaced with tubing coated with PVA-containing SNP (FIG. 1, point B). This resulted in an immediate relaxation of the pre-contracted pulmonary artery ring, reaching 50% relaxation in approximately 10 minutes (FIG. 1). Replacing this tubing with control tubing and washing with MKS, returned the tension to the pre-contracted state. These data demonstrate that release of nitric oxide from PVA-containing SNP promotes relaxation of this tissue.

Example 4

Figure 2:
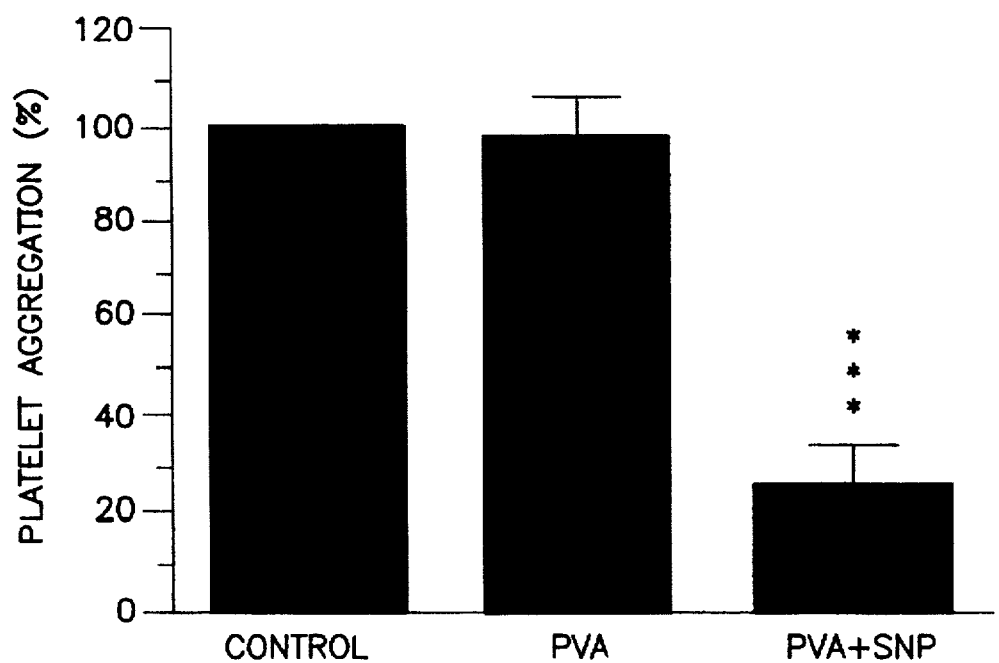
FIG. 2 is a graph of platelet aggregation in treated and untreated tubes.
Figure 3:
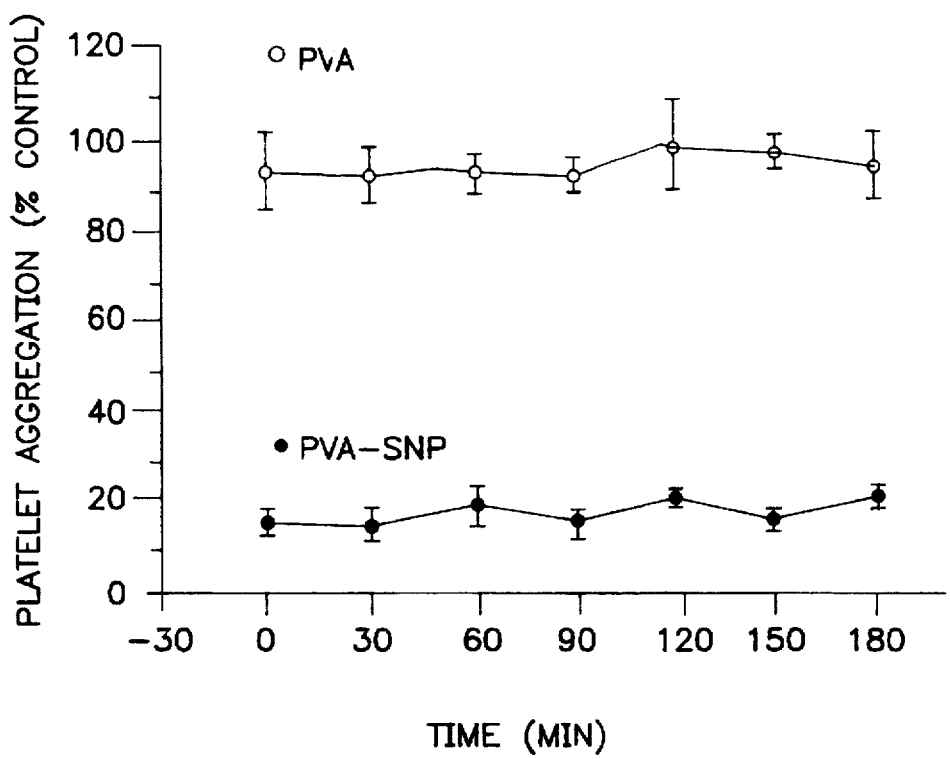
FIG. 3 is a graph of platelet aggregation over time in treated and untreated tubing.
Figure 4:
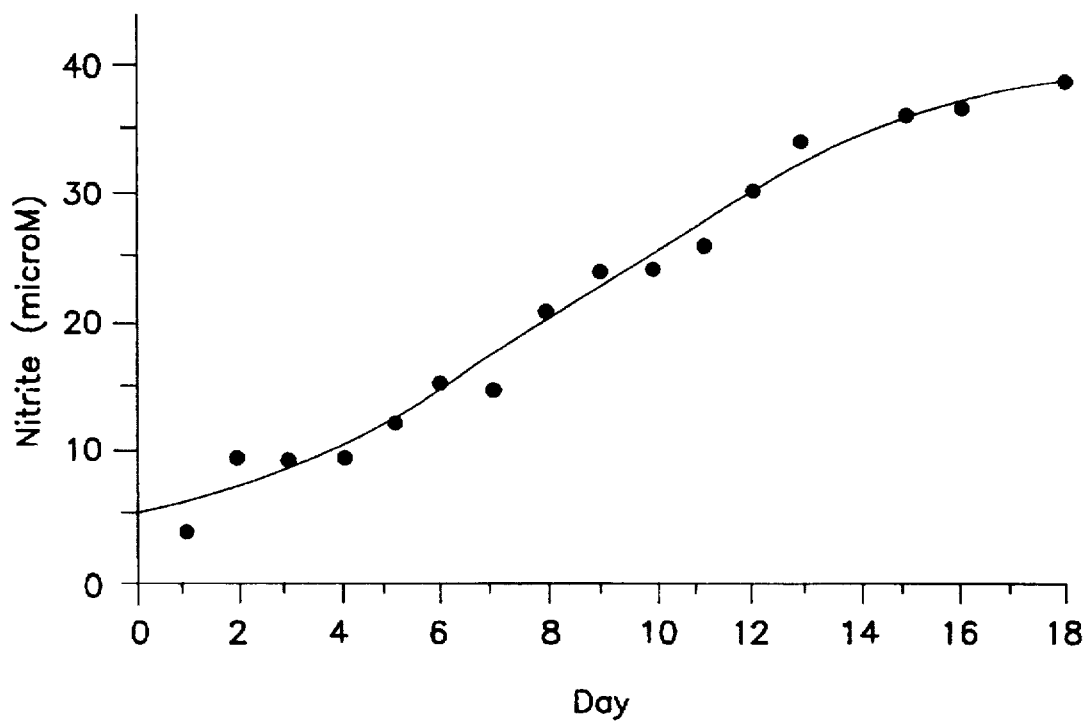
FIG. 4 is a graph of nitro-prusside release from treated tubing.

Biologic Assay for Nitric Oxide—Platelet Aggregation. Optimal aggregation of human platelets was measured with a four-channel platelet aggregometer (Model 560-Ca, Chromo-log, Havertown, Pa.). Venous blood was collected in a citrated tube, centrifuged at 250×g to isolate platelet rich plasma (PRP, platelet count was approximately 300,000/mL). Platelet aggregation was induced by ADP (10 μM, final concentration). In experiments with coated tubes, plasma was placed into control Falcon tubes (no coating), PVA-coated Falcon tubes without SNP and PVA-coated Falcon tubes-containing SNP, respectively for 3 minutes. As can be seen in FIG. 2, only the tube coated with PVA-containing SNP prevent platelet aggregation. We next explored the time course of this reaction. In a different series of experiments, inhibition of platelet aggregation was set at 70% (at time zero), which continued for three hours (FIG. 3). Identical results were obtained using polyvinyl chloride coated tubing. These results demonstrate that release of nitric oxide from tubes with PVA-containing SNP continues for at least three hours. Using the same experimental design, we have found that release of nitric oxide from these tubes can continue for at least 18 days (FIG. 4). Each data point in FIG. 4 represents an accumulation of nitric oxide released over the 18 day study. Each point is the summation of the concentration of nitric oxide released over the previous 24 hour period plus the total amount released to that day. Changing to polyvinyl chloride coated tubing leads to even more superior results over a period of time reaching 30 days. Contrast these results with the well established in vivo findings of a nitroprusside (SNP) lifetime in minutes (Palmer and Lasseter, New Engl. J. Med. 292: 294–297, 1975; Packer, Meller, Medine, Gorlin and Herman, New Engl. J. Med. 301: 1193–1197, 1979).

Example 5

To prepare a polymer coated stent, a stainless steel stent (90 mm diameter; 28 mm in length, formed of interwoven 0.17 mm stainless stell wire) is placed in a solution of polyvinyl alcohol, prepared as described in Example 1, to which nitroprusside (SNP) was added to reach a final concentration of 10 μM. After air drying the stent, this leaves a translucent SNP-containing PVA film as a coating on the walls of the stent and an interstitial membrane enveloping the stent. Verification that the nitric oxide releasing compounds is present in the coated stent is based on measuring nitric oxide release, when the PVA-coated stent is placed in phosphate buffer, pH 7.4 using the Griess reaction (Green, Wagner, Giowski, Skipper, Wishnok and Tannebaum, Anal. Biochem. 126: 131–138, 1982).

Example 6

An angioplasty balloon device, comprising a catheter, wires and balloon, coated with a coating of polyvinyl alcohol or polyvinyl chloride containing 1–100 μmoles of nitroprusside (SNP) as the nitric oxide-releasing compound, is delivered to the appropriate arterial site using standard angioplasty techniques. After expansion of the balloon for about 10 minutes, the balloon is then deflated and the device removed. The nitric oxide released from the device during angioplasty procedure inhibits platelet adhesion to the site of angioplasty.

Example 7

The interior surface of tubing used to transport blood from and back to a patient undergoing hypothermic surgery utilizing cardiac and/or pulmonary bypasses or dialysis is coated by filling the tubing with an aquous/THF solution of nitroprusside in polyvinyl alcohol or polyvinyl chloride at room temperature until the inner surface of the tubing is coated with this mixture. Tubing, thus treated, inhibits platelet aggregation in the blood of the patent undergoing hypothermic surgery or dialysis.

The preceding examples can be repeated with similar success by substituting the generically or specifically described reactants and/or operating conditions of this invention for those used in the preceding examples. For example, the tip of a catheter used to scrape a deposit from the interior wall of an artery can similarly be coated.

What is claimed is:

1. In a method for producing a medical device capable of inhibiting the aggregation of platelets from blood flowing in a living being resulting from exposure of the blood to a medical device by coating the surface of the foreign body prior to contact therewith, with a physiologically acceptable polymer coating which contains dissolved or dispersed therein a therapeutic drug, the improvement wherein the polymer coating is insoluble in the blood and has a porosity sufficiently small to inhibit diffusion of blood-borne reductants from entering the coating and sufficiently large to allow passive diffusion of nitric oxide from within the polymer coating into the blood stream of the living being and contains dissolved or dispersed therein as the therapeutic drug and the source of the nitric oxide an amount of a nitrosyl-containing organometallic compound, which slowly decomposes at body temperature within the polymer coating when the device is exposed to the blood stream of the living being and in so doing releases from the coating into the blood stream an amount of nitric oxide effective to inhibit platelet aggregation which would otherwise be promoted by contact of the blood with the foreign body.

2. A method according to claim 1, wherein the living being is a human.

3. A method according to claim 2, wherein the foreign body is an intravascular device adapted to be inserted surgically into a blood vessel of a human in conjunction with percutaneous transluminal coronary angioplasty.

4. A method according to claim 3, wherein the foreign body is a stent.

5. A method according to claim 4, wherein the coating is applied to all of the exposed surfaces of the stent.

6. A method according to claim 5 wherein the nitrosyl containing organometallic compound is nitroprusside and the amount of nitric oxide released from the polymer coating is effective to prevent restenosis.

7. A method according to claim 2, wherein the foreign body is the inner surface of plastic tubing adapted to transport blood of a patient undergoing hypothermic surgery or dialysis.

8. A method according to claim 2, wherein the foreign body is a balloon, a catheter or a stent adapted to be inserted surgically into a blood vessel of a human in conjunction with transluminal coronary angioplasty, and the nitric oxide releasing compound is nitroprusside.

9. A method according to claim 2, wherein the organometallic compound is nitroprusside.

10. A method according to claim 2 wherein the foreign body is plastic tubing adapted to transport a stream of blood, the nitrosyl-containing organometallic compound is nitroprusside and the amount of nitric oxide released from the polymer coating is effective to prevent thrombotic occlusion.

11. In a device adapted for exposure to blood flowing in a living being, said device having an exterior surface coated with a coating of a physiologically acceptable polymer which contains dissolved or dispersed therein a therapeutic drug, the improvement wherein the polymer coating is insoluble in the blood and has a porosity sufficiently small to inhibit diffusion of blood-borne reductants from entering the coating and sufficiently large to allow passive diffusion of nitric oxide from within the polymer coating into the blood stream of the living being and contains dissolved or dispersed therein as therapeutic drug and the source of the nitric oxide an amount of a nitrosyl-containing organometallic compound which slowly at the body temperature of the living being decomposes within the polymer coating when the device is exposed to the blood of the blood stream of the living being and in so doing releases from the coating into the blood stream an amount of nitric oxide at a rate effective to mediate the platelet aggregation which could otherwise occur after the device is exposed to the blood.

12. A stent according to claim 11, wherein the nitrosyl-containing organometallic compound, is nitroprusside.

13. A device according to claim 11, which is an intravascular device adapted for insertion into the blood stream of the living being and whose exterior surfaces which are exposed to the blood are coated with the polymer coating.

14. An intravascular device according to claim 13, which is a stent.

15. A device according to claim 11, which is an extravascular device comprising plastic tubing adapted for transporting the blood of a living being and whose inner surface is coated with the polymer coating.

16. An extravascular device according to claim 15, wherein the organometallic compound is nitroprusside.

* * * * *